US006312953B1

(12) United States Patent
Meyer, Jr. et al.

(10) Patent No.: US 6,312,953 B1
(45) Date of Patent: *Nov. 6, 2001

(54) BIFUNCTIONAL CROSSLINKING OLIGONUCLEOTIDES ADAPTED FOR LINKING TO A TARGET SEQUENCE OF DUPLEX DNA

(75) Inventors: Rich B. Meyer, Jr.; Howard B. Gamper, both of Woodinville; Igor V. Kutyavin; Alexander A. Gall, both of Bothell, all of WA (US)

(73) Assignee: Epoch Pharmaceuticals, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/266,949

(22) Filed: Jun. 27, 1994

Related U.S. Application Data

(63) Continuation-in-part of application No. 08/011,482, filed on Jan. 26, 1993, now abandoned.

(51) Int. Cl.$^7$ .............................. C12Q 1/68; C07H 21/04
(52) U.S. Cl. ............................ 435/375; 435/6; 435/91.1; 435/440; 435/325; 536/23.1; 536/24.3; 536/24.5
(58) Field of Search .............................. 514/44; 536/24.3, 536/24.5, 24.31, 24.32, 18.4, 124; 435/6, 91.1, 440, 325, 375, 326, 377; 436/94, 183

(56) References Cited

U.S. PATENT DOCUMENTS 5,176,996    1/1993    Hogan et al. .............................. 436/6

FOREIGN PATENT DOCUMENTS

| 0375408 | 6/1990 | (EP) | .............................. | C12N/15/10 |
| WO90/14353 | 11/1990 | (WO) | .............................. | C07H/21/00 |
| WO90/15884 | 12/1990 | (WO) | .............................. | C12Q/1/68 |
| WO91/18997 | 12/1991 | (WO) | .............................. | C12P/19/34 |
| WO92/20698 | 11/1992 | (WO) | .............................. | C07H/21/04 |

OTHER PUBLICATIONS

J. Milligan et al. J. Med. Chem. 36(14) 1923–37 ('93).*
B. Tseng et al. Cancer Gene Therap. 1(1):65–71 ('94).*
M. Podyminogen et al. Biochem. 34:13098–13108 ('95).*
R. Stull et al. Pharm. Res. 12(4) 465–83 ('95).*
L. J. Maher, III. Bioessays 14(12) 807–15 ('92).*
Genesis Group Associates, Inc., Dialog Abstract # 01997756, File 636('93).*
H. Moser et al. Science 238 ('87) pp. 645–650.*
D. Praseuth et al. PNAS 85:1349–53 ('88).*
N. Sats et al., Bioorg. Khimiya 14(9) 1188–95 ('88) Russian.*
C. Stein et al. Science 261:1004–12 ('93) See Translation.*
J. Hartley et al. Biochem, vol. 29 (1990) pp. 2985–2591.*
C. Stein et al. Science, vol. 261 ('93) pp. 1004–1012.*
R. Weiss Science News, vol. 139 (91) pp. 108–109.*
J. Sats et al. abstract Bioorg. Khim. vol. 14(9) pp. 1188–1196.*
X–B. Kong et al. (abstract) Molecular Pharmacology, vol. 41(9) ('92) pp. 237–244.*
H. Moser et al. Science, vol. 238 ('87) pp. 645–650.*
Morris J. Robins, et al., "Nucleic Acid related Compounds. 39. Efficient Confersion of 5–Iodo to 5–Alkynyl and Derived 5–Substituted Uracil Bases and Nucleosides", J. Org. Chem., 1983, 48, pp. 1854–1862.
Rainer John, et al., "Synthese von Sieben–und Achtring–a–nellierten Pyridinen durch inverse intramolekulare Diels–Alder–Reaktion mit Trifluormethyl–substituierten 1,2, 4–Triazinen", Chem. Ber., 123, (1990), 133–136.
Morris J. Robins, et al., "Nucleic acid related compounds. 38. Smooth and high–yield iodination and chlorinatic at C–5 uracil bases and p–toluyl–protected nucleosides", Can. J. Chem., vol. 60, 1982, pp. 554–557.
Moneesh Chatterjee, et al., "Inducible Alkylation of DNA Using an Oligonucleotide–Quinone Conjugate", J. Am. Chem. Soc., 1990, 112 pp. 6397–6399.
Jeng–Pying Shaw et al., "Specific, High–Efficiency, Triple–Helix–Mediated Cross–Linking to Duplex DNA", J. Am. Chem. Soc., 1991, 113, pp. 7765–7766.
Brent L. Iverson, et al., "Nonenzymatic sequence–specific methyl transfer to single–stranded DNA", Proc. Natl. Acad. Sci, U.S.A., vol. 85, Jul. 1988, pp. 4615–4619.

(List continued on next page.)

Primary Examiner—John L. LeGuyader
(74) Attorney, Agent, or Firm—Klein & Szekeres, LLP

(57) ABSTRACT

Chemically modified oligonucleotides (ODNS) are complementary, either in the sense of the classic "four letter code" recognition motif, or in the sense required for triple strand formation based on the more limited "two letter code recognition motif", to a target sequence of double stranded DNA of an invading cell, organism or pathogen, such as a virus, fungus, parasite, bacterium, malignant cell, or any duplex DNA which is desired to be broken into segments for the purpose of "mapping". The ODNs have cross-linking agents covalently attached at least to two different sites of the ODN. Alternatively, the cross-linking agent which is attached to one site on the ODN has two cross-linking functionalities, and therefore in effect comprises two cross-linking agents. The cross-linking agent typically includes a linker arm (such as an alkyl, alkoxy, aminoalkyl or amidoalkyl chain) and a reactive group which, after triple strand formation with the target sequence of DNA, is capable of reacting with the target DNA to form a covalent bond therewith. Each cross-linking agent of the novel modified ODNs is capable of forming a covalent bond with the target DNA. As a result of the covalent bond formation between the modified ODN and both strands of the target DNA sequence, replication and expression of the target DNA sequence is inhibited. Alternatively the duplex DNA is selectively cleaved with enzymes or amino acids, at the alkylation sites for "mapping" or other investigative purposes.

30 Claims, 1 Drawing Sheet

OTHER PUBLICATIONS

Thomas R. Webb, et al., "Hybridization triggered cross–linking of deoxyoligonucleotides", *Nucleic Acids Reseach.*, vol. 14, No. 19, 1986, pp. 7661–7675.

James Summerton, et al., "Sequence–specific Crosslinking Agents for Nucleic Acids", *Mol. Biol.*, (1978), 122, pp. 145–162.

Dmitri G. Knorre, et al., "Complementary–Addressed (Sequence–Specific) Modification of Nucleic Acids", *Progess in Nucleic Acid Research and Molecular Biology*, vol. 32, 1985, pp. 291–320.

Paul C. Zamecnik, et al., "Inhibition of replication and expression of human T–cell lymphotropic virus type III in cultured cells by exogenous synthetifc oligonucleotides complementary to viral RNA" *Proc. Natl. Acad. Sci, U.S.A.*, vol. 83, Jun. 1986, pp. 4143–4146.

Mary L. Stephenson, et al., "Inhibition of Rous sarcoma viral RNA translation by a specific oligodeoxyribonucleotide", *Proc. Natl. Acad. Sci. U.S.A.*, vol. 75, No. 1, Jan. 1978, pp. 285–288.

Frank M. Orson, et al., "Oligonucleotide inhibition of 1L2Ra mRNA transcription by promoter region collinear triplex formation in lymphocytes", *Nucleic Acids Reseach*, vol. 19, No. 12, May 17, 1991, pp. 3435–3441.

Roger A. Jones, "Preparation of Protected Deoxyribonucleosides", Oligonucleotide synthesis, *Practical Approac Series, IRL, Press*, Chapter 2, pp. 23–34.

E. Sonveaux, "Reviews: the Organic Chemistry Underlying DNA Synthesis", Bioorganic Chemistry, vol. 14, (1986), pp. 274–325.

Scott W. Umlaut, et al., "Triple–helical DNA Pairing Intermediates Formed by recA Protein", The Journal of Biological Chemistry, vol. 265, No. 28, Issue of Oct. 5, 1990, pp. 16898–16912.

Nguyen Tanh Thuong, et al., "Chamical synthesis of natural and modified oligodeoxynucleotides", *Biochime*, vol. 67, 1985, pp. 673–684.

Kathleen R. Blake, et al., "Hybridization Arrest of Globin Synthesis in Rabbit Reticulocyte Lysates and Cells by Oligodeoxyribonucleoside Methylphosphonates", *Biochemistry*, vol. 24, 1985, pp. 6139–6145.

Paul C. Zamecnik, et al., "Inhibition of Rous sarcoma virus replication and cell transformation by a specific oligodeoxynucleotide", *Proc. Natl. Acad. Sci. U.S.A.*, vol. 75, No. 1, Jan. 1978, pp. 280–284, Biochemistry.

D.G. Korre, et al., "Oligonucleotides Linked to Reactive Groups", Ed. by J. Cohen, Chapter 8, CRC Press, Inc., 1989, pp. 173–196.

Rich B. Meyer, et al., "Efficient, Specific Cross–Linking and Cleavage of DNA by Stable, Synthetic Complementary Oligodeoxynucleotides", *J. Am. Chem. Soc.*, vol. 111, (1989), pp. 8517–8519.

Trung Le Doan, et al., "Sequence–specific recognition, phorocross–linking and cleavage of DNA double helix by an oligo–[a]–thymidylate covalently linking to a azidoproflavine dervative", *Nucleic Acids Research*, vol. 15, No. 19, (1987), pp. 7749–7760.

Eugen Uhlmann et al., "Antisense Oligonucleotides: A New Therapeutic Principles" *Chemical Reviews.* vol. 90. No. 4, (Jun. 1990), pp 543–584.

Russell O. Pieper, et al., "Transcription–terminating lesions induced by bifunctional alkylating agents in vitro", *Carcinogenesis*,vol. 10, No. 7, pp. 1307–1314 (1989).

* cited by examiner

BIFUNCTIONAL CROSSLINKING OLIGONUCLEOTIDES ADAPTED FOR LINKING TO A TARGET SEQUENCE OF DUPLEX DNA

CROSS-REFERENCE TO RELATED APPLICATION

The present application is a continuation-in-part of application Ser. No. 08/011,482, filed on Jan. 26, 1993, now abandoned.

The U.S. Government has a nonexclusive, nontransferable, irrevocable paid-up license to practice or have practiced this invention for or on its behalf as provided for by the terms of Contract DAMD 17-88-C-8201 awarded by the U.S. Department of the Army.

BACKGROUND OF THE INVENTION

1. Field of the Invention

The present invention is directed to oligonucleotides which are capable of binding by H-bonding to a target sequence of nucleotides in the double stranded DNA of an invading organism, such as a virus, fungus, parasite, bacterium or tumor cell, and which carry at least two covalently linked electrophilic groups which after hybridization covalently bind to the target sequence of nucleotides, with the result that replication and/or expression of the target sequence is prevented. Alternatively, the oligonucleotides of the present invention can bind in vitro by H-bonding to a target sequence of duplex DNA which is to be cleaved at the target location. Alkylation of both strands of the duplex DNA enhances its susceptibility to cleavage at the alkylation sites and therefore provides a tool for DNA mapping or similar investigative or analytical purposes.

2. Description of the Prior Art

Oligodeoxynucleotides (ODNs) have great potential as sequence specific pharmaceutical agents for the inhibition of gene expression. Chemically synthesized ODNs may inhibit the expression of specific gene products through formation of duplexes upon hybridization with complementary messenger RNAs (mRNAs). More specifically, these "antisense" ODNs are believed to inhibit the processing or translation of message primarily through an RNase H-mediated cleavage of the target mRNA sequence. Because of this inhibitory effect, antisense ODNs may be useful as anti-viral, anti-parasitic, and anti-cancer agents. However, "antisense" technology is beset with certain fundamental disadvantages relating, for example, to degradation of antisense ODNs by nuclease enzymes, and uptake (or lack of uptake) by cells. To improve their properties, modified antisense ODNs, such as ODNs with modified backbones (oligonucleoside methylphosphonates and phosphorothioates) have been prepared. It has been found however, that improvement in some properties, such as resistance to nuclease enzymes frequently has deleterious effects on other properties, such as cellular uptake and loss of specificity.

Another approach to improve the effectiveness of antisense ODNs involves covalently attaching moieties to the antisense ODNs which moieties interact directly with the target RNA upon hybridization and therefore potentiate the antisense activity of the ODN. Groups employed in this regard are intercalating groups, and groups which covalently link with the target RNA after hybridization.

Anti-gene ODNs

A variation of the "antisense" approach to rational drug design is termed "anti-gene". Whereas antisense ODNs target single stranded MRNA, anti-gene ODNs hybridize with and are capable of inhibiting the function of double-stranded DNA. More specifically, anti-gene ODNs form sequence-specific triple-stranded complexes with a double stranded DNA target and thus interfere with the replication or transcription of selected target genes. As is known, except for certain RNA viruses and nucleic acid-free viroids, DNA is the repository for all genetic information, including regulatory control sequences and non-expressed genes, such as dormant proviral DNA genomes. In contrast, the target for antisense ODNs, MRNA, represents a very small subset of the information encoded in DNA. Thus, anti-gene ODNs have broader applicability and are potentially more powerful than antisense ODNs that merely inhibit mRNA processing and translation.

Anti-gene ODNs in the nuclei of living cells can form sequence-specific complexes with chromosomal DNA. The resultant triplexes have been shown to inhibit restriction and/or transcription of the target double stranded DNA. Based on the known stabilities of the two target nucleic acid species (i.e., DNA and RNA), anti-gene interference with DNA functioning has longer lasting effects than the corresponding antisense inhibition of mRNA function.

Anti-gene therapy may be based on the observation that under certain conditions DNA can form triple-stranded complexes. In these triple-standed complexes, the third strand resides in the major groove of the Watson-Crick base paired double helix, where it hydrogen bonds to one of the two parental strands. A binding code governs the recognition of base pairs by a third base (see allowed triplets below, Hoogsteen pairing). In each case, the third strand base is presented first and is followed by the base pair in the Watson-Crick duplex.

| allowed triplets: | A-A-T | G-G-C |
|---|---|---|
| | T-A-T | C-G-C |

Certain limitations of this base pair recognition code are apparent from the allowed triplets. First, there is no capability for the recognition of T-A and C-G base pairs; hence, triple strand formation is restricted to runs of homopurine bases on one strand and homopyrimidine bases on the other strand of the duplex. In other words, the third strand or ODN binds only to one strand of the duplex and can only bind to purines. Second, if cytosine is in the third strand ("C"), it must be protonated to be able to hydrogen bond to the guanine of a G-C base pair. The pKa for protonation of cytosine is 4.6, suggesting that at physiological pH the stability of C-G-C triads is likely to be impaired. Third, in all cases triads are maintained by two hydrogen bonds between the third strand base and the purine residue of the duplex base pair. Hence, triple-stranded complexes are generally less stable than the parental double-stranded DNA, which is maintained by a combination of two (A-T) or three (G-C) hydrogen bonds between purine and pyrimidine pairs. (Watson-Crick motif).

An important disadvantage of triple strand formation as discussed above is the relatively slow kinetics of triple strand formation. However, triple strand formation can be catalyzed in cells by recombinase enzymes which are practically ubiquitous in cells and whose existence is well known in the art. In addition to a much faster rate of triple strand formation, recombinase enzyme-catalyzed triple strand formation also provides the advantage of universal sequence recognition (in contrast to the A-T and G-C recognition limitation associated with non-enzyme-mediated triple strand formation). More specifically, the recombinase enzyme-mediated recognition motif recognizes all four base pairs, thereby allowing targeting of any double stranded DNA sequence. Second, the nucleoprotein filament, which is the complex formed between a recombinase enzyme and the single-stranded ODN, searches for target double strand DNA homology much more efficiently than does a small naked anti-gene ODN, thus decreasing the concentration of anti-gene ODN required for efficient triple strand complex formation. Third, due to the hydrogen bonding patterns and the novel helical twist involved in enzyme-mediated recognition, the resultant triple strand complex is stable at physiological pH. Fourth, since the cellular recombinational pathway is being harnessed, the DNA in higher order chromatin structures will be accessible for targeting.

The ability to conduct an efficient homology search is a significant advantage. Preliminary data (F. M. Orson et al., *Nucl. Acids Res.* 19:3435–41, 1991) indicate that ODNs are inefficient at scanning double stranded DNA for complementary homopurine sequences. In contrast, a classical hybridization between two complementary single strands would occur within seconds, rather than hours. Since the human genome contains over $3 \times 10^9$ base pairs, the homology search time may be inordinately long, especially if anti-gene ODNs are used at relatively low concentration. The use of presynaptic nucleoprotein filaments, such as those formed between single stranded DNA and recA, that bind weakly to and move rapidly along double stranded DNA effectively reduces the homology search from a three dimensional to a two dimensional process. Furthermore, upon homologous registry with the double strand, the nucleoprotein filament will more likely produce a triple strand complex than the corresponding interaction of double strand and a naked single strand.

Because of these factors, triple strand formation between a recA-coated, single stranded ODN and an homologous double strand occurs at a reaction rate that exceeds by 1 or 2 orders of magnitude the calculated rate of spontaneous renaturation of complementary single strands under standard hybridization conditions.

A first demonstration of the concept of using sequence-specific, antisense oligonucleotides as regulators of gene expression and as chemotherapeutic agents was described by Zamecnik and Stephenson, *Proc. Natl. Acad. Sci. USA,* 75:280 (1978). These authors showed that a small antisense oligodeoxynucleotide probe can inhibit replication of Rous Sarcoma Virus in cell culture, and that RSV viral RNA translation is inhibited under these conditions (Stephenson et al., *Proc. Natl. Acad. Sci. USA* 75:285 (1978)). Zamecnik et al., *Proc. Natl. Acad. Sci. USA,* 83:4143 (1986), have also shown that oligonucleotides complementary to portions of the HIV genome are capable of inhibiting protein expression and virus replication in cell culture. Inhibition of up to 95% was obtained with oligonucleotide concentrations of about 70 µM. Importantly, they showed with labeled phosphate studies that the oligonucleotides enter cells intact and are reasonably stable to metabolism.

The concept of covalently linking an inhibitor molecule to a target (such as binding an ODN to an target sequence with a cross-linking arm,) is related to the pioneering work of B. R. Baker, "Design of Active-Site-Directed Irreversible Enzyme Inhibitors," Wiley, New York, (1967), who used what was termed "active-site-directed enzyme inhibitors" in chemotherapeutic applications. The concept of incorporating a crosslink in an oligonucleotide has been sporaidically discussed by several authors. For example, Knorre and Vlassov, Prog. Nucl. Acid Res. Mol. Biol., 32:291 (1985), have discussed sequence-directed crosslinking ("complementary addressed modification") using an N-(2-chloroethyl)-N-methylaniline group attached to either the 3'- or 5'-terminus of oligonucleotides. Summerton and Bartlett, *J. Mol. Biol.,* 122:145 (1978) have shown that an 8-atom chain, attached to a cytosine residue at its C-4 position and terminating in the highly reactive bromomethyl ketone group, can crosslink to the N-7 of guanosine. Webb and Matteucci, *Nucleic Acids Res.,* 14:7661 (1986), have prepared oligonucleotides containing a 5-methyl-N,N-ethanocytosine base which is capable of slow crosslinking with a complementary strand. In a conceptually related alkylation via a linker arm within a DNA hybrid, Iverson and Dervan, *Proc. Natl. Acad. Sci. USA,* 85:4615 (1988), have shown opposite strand methylation, triggered by BrCN activation of a methylthio ether, predominately on a guanine base located two pairs from the base bearing the linker. Vlassov et al. in *Gene* 72 (1988) 313–322, describe sequence specific binding and alkylation of plasmid DNA with oligodeoxynucleotide derivatives containing 2-chloroethyl-N-methyl amino phenyl residues. Similar cross-linking, using different cross-linking agent was described by Shaw et al., *J. Am.Chem. Soc.* 1991, 113, 7765–7766.

Further information pertaining to ODNs, chemically modified ODNs and their ability to affect or inhibit replication or translation of a target sequence of DNA or RNA can be found in European Patent Application No. 86309090.8, PCT publication WO8707611, U.S. Pat. No. 4,599,303, EP 0259186, PCT publication WO8503075, German Patent DE3310337, and in the publications Blake et al., *Biochemistry* 24:6139 (1985); Umlauf et al., "Triple-helical DNA Pairing Intermediates Formed by recA Protein,", *Biol. Chem.,* 265(28), 16898–16912 (1990); and Thuong et al., "Chemical synthesis of natural and modified oligodeoxynucleotides.", *Biochimie,* 1985, 67, 673–684.

DNA Mapping

In addition to chemotherapy or potential chemotherapy utilizing ODNs or modified ODNS, a broad field has developed in the prior art for DNA mapping (gene mapping), that is, for in vitro determination of DNA sequence or partial DNA sequence. An important step in such DNA sequencing (gene mapping) is the cleavage of the target DNA into smaller fragments. The modified ODNs of the present invention also have utility in this field.

SUMMARY OF THE INVENTION

The present invention relates to chemically modified oligonucleotides (ODNs) which are complementary, either in the sense of the classic "four letter code" recognition motif, or in the sense required for triple strand formation based on the more limited "two letter code recognition motif", to a target sequence of DNA. The target DNA may be in an invading cell, organism or pathogen, such as a virus, fungus, parasite, bacterium or malignant cell. The target DNA may also be a gene or other duplex DNA which is to be sequenced ("mapped") or otherwise analyzed or investigated in vitro. The ODNs have cross-linking agents covalently attached at least to two different sites of the ODN. Alternatively, the cross-linking agent which is attached to one site on the ODN has two cross-linking functionalities, and therefore in effect comprises two cross-linking agents. The cross-linking agent typically includes a linker arm (such as an alkyl, alkoxy, aminoalkyl or amidoalkyl chain) and a reactive group which, after triple strand formation with the target sequence of DNA, is capable of reacting with the target DNA to form a covalent bond therewith. Each cross-linking agent of the novel modified ODNs is capable of forming a covalent bond with the target DNA. As a result of the covalent bond formation between the modified ODN and the target DNA sequence, replication and expression of the target DNA sequence is inhibited. The novel ODNS can also be used to create sites for cleavage on both strands of a target DNA at specific target locations and thereby provide a useful tool for DNA sequencing, gene mapping and related in vitro analytical procedures.

The ODNs of the present invention, in addition to having at least two covalently attached cross-linking agents, may also have other modifications, such as modifications of the heterocyclic bases, of the sugar as well as of the phosphate moieties, relative to naturally occurring ribonucleotides and deoxyribonucleotides. The cross-linking agents may be attached to either the heterocyclic bases, to the sugars or modified sugars, or to the phosphate or modified phosphate moieties.

The present invention also relates to the methods of using the novel ODNs in combination with cell indigenous recombinase enzymes.

DETAILED DESCRIPTION OF THE INVENTION

General Embodiments

Figure 1:
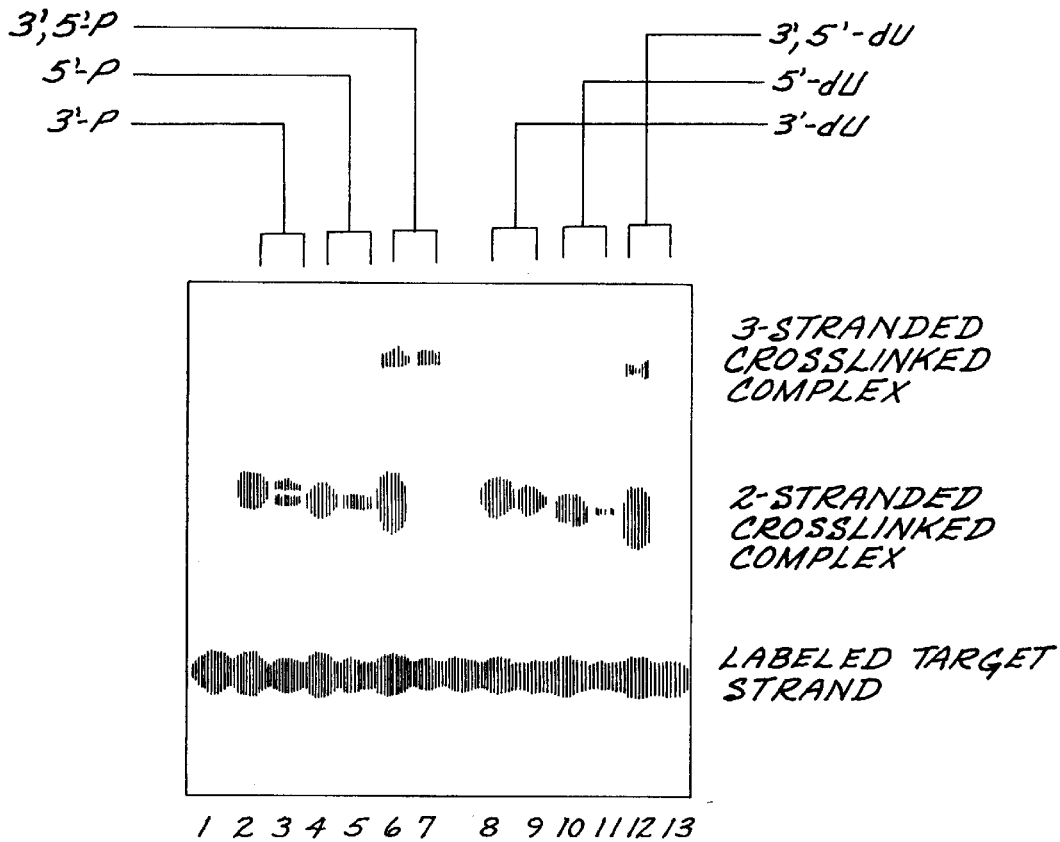
FIG. 1 is an illustration of polyacrylamide gel electrophoresis performed to demonstrate cross-linking of both strands of duplex DNA with the oligonucleotide of the present invention.
Figure 1:
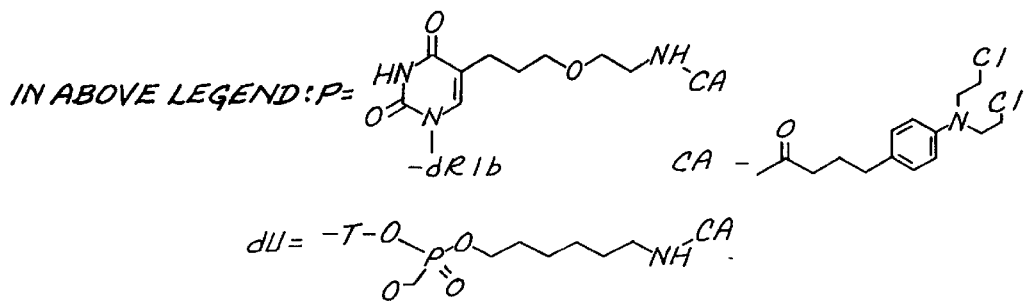

As is known in the art, oligonucleotides (ODNs) comprise a chain of nucleotides which are linked to one another by phosphate ester linkages. Each nucleotide typically comprises a heterocyclic base (nucleic acid base), a sugar moiety attached to the heterocyclic base, and a phosphate moiety which esterifies a hydroxyl function of the sugar moiety. The principal naturally occurring nucleotides include uracil, or thymine, cytosine, adenine and guanine as the heterocyclic bases, and ribose or deoxyribose as the sugar moiety. The foregoing brief summary of basic nucleotide and oligonucleotide structural chemistry is mentioned because, in accordance with the present invention, at least two chemical cross-linking agent groups are attached to an oligonucleotide which is complementary to a target sequence of double stranded DNA.

The oligonucleotide of the invention may comprise ribonucleotides (containing ribose as the only or principal sugar component), deoxyribonucleotides (containing deoxyribose as the principal sugar component), or in accordance with established state-of-the-art modified sugars or sugar analogs may be incorporated in the ODN of the present invention. Thus, in addition to ribose and deoxyribose, the sugar moiety may be pentose, deoxypentose, hexose, deoxyhexose, glucose, arabinose, xylose, lyxose, and a sugar "analog" cyclopentyl group. The sugar may be in a pyranosyl or in a furanosyl form. In the modified ODNs of the present invention the sugar moiety is preferably the furanoside of ribose, deoxyribose, arabinose or 2'-O-methylribose, and the sugar may be attached to the respective heterocyclic bases either in α or β anomeric configuration. The preparation of these sugars or sugar analogs and of the respective "nucleosides" wherein such sugars or analogs are attached to a heterocyclic base (nucleic acid base) per se is known, and need not be descibed here, except to the extent such preparation may pertain to any specific example.

The phosphorous derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate, phosphorodithioate or the like. The preparation of the above-noted phosphate analogs, and their incorporation into nucleotides, modified nucleotides and ODNs, per se, is also known and need not be descibed here. Preferably, the phosphate derivative incorporated into the therapeutic oligonucleotides of the present invention is a "simple" phosphate, which in an internucleotidic bond forms a phosphate diester, and which at the 3' and 5' ends of the modified ODNs of the invention may carry the cross-linking agent. In this regard it is noted that recombinase enzymes are believed to recognize such "simple" phosphates and deoxyribose backbones. The cross-linking agent is described in substantial detail below.

The heterocyclic bases, or nucleic acid bases which are incorporated in the modified ODNs of the present invention may be the naturally occurring principal purine and pyrimidine bases, (namely uracil, or thymine, cytosine, adenine and guanine, as mentioned above), as well as naturally occurring and synthetic modifications of said principal bases. Those skilled in the art will recognize that a large number of "synthetic" non-natural nucleosides comprising various heterocyclic bases and various sugar moieties (and sugar analogs) have become available in the prior art, and that as long as other criteria of the present invention (such as being "complementary to a target sequence of DNA) are satisfied, the novel ODNs of the invention may include one or several heterocyclic bases other than the principal five base components of naturally occurring nucleic acids. Preferably, however, the heterocyclic base in the modified ODNs of the present invention is selected from uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrrolo[2,3-d]pyrimidin-5-yl, 4-aminopyrazolo[3,4-d]pyrimidin-3-yl or 4-amino-6-oxopyrazolo[3,4-d]pyrimidin-3-yl groups, where the purines are attached to the sugar moiety of the oligonucleotides via the 9-position, the pyrimidines via the 1-position, the pyrrolopyrimidines via the 7-position and the pyrazolopyrimidines via the 1-position.

The cross-linking agents incorporated in the present invention need to meet the requirements that (1) each cross-linking agent must be covalently bonded to a site on the ODN, (2) its length and steric orientation must be such that it can reach a suitable reaction site in the target DNA sequence after the ODN is hybridized with the target (with or without the assistance of a recombinase enzyme) (3) and must have a reactive group which will react with a reactive group of the target DNA sequence. As noted above, the cross-linking agents may be covalently attached to the heterocyclic bases, to the sugar or modified sugar residues, or to the phosphate or modified phosphate functions of the ODNs. Any combination of the attachment of two or more cross-linking agents to the ODN is within the scope of the present invention.

In the simplest terms the cross-linking agent itself may conceptually be divided into two groups or moieties, namely the reactive group, which is typically and preferably an electrophilic leaving group (L), and an "arm" (A) which attaches the leaving group L to the respective site on the ODN. The leaving group L may be chosen from, for example, such groups as chloro, bromo, iodo, $SO_2R'''$, or $S^+R'''f'''$, where each of $R'''$ and $R''''$ is independently $C_{1-6}$alkyl or aryl or $R'''$ and $R''''$ together form a $C_{1-6}$alkylene bridge. Chloro, bromo and iodo are preferred. Within these groups haloacetyl groups such as —$COCH_2I$, and bifunctional "nitrogen mustards", such as —N—$[(CH_2)_2$—$Cl]_2$ are preferred. The leaving group will be altered by its leaving ability. Depending on the nature and reactivity of the particular leaving group, the group to be used is chosen in each case to give the desired specificity of the irreversibly binding probes.

Although as noted above the "arm" (or linker arm) A may conceptually be regarded as a single entity which covalently bonds the ODN to the leaving group L, and maintains the leaving group L at a desired distance and steric position relative to the ODN, in practice the "arm" A may be constructed in a synthetic scheme where a bifunctional molecule is covalently linked to the ODN (for example by a phosphate ester bond to the 3' or 5' terminus, or by a carbon-to-carbon bond to a heterocyclic base) through its first functionality, and is also covelently linked through its second functionality (for example an amine) to a "hydrocarbyl bridge" (alkyl bridge, alkylaryl bridge or aryl bridge, or the like) which, in turn, carries the leaving group.

A general formula of the cross linking function is thus —A—L, or —A—$L_2$ where L is the above defined leaving group and A is a moiety that is covalently linked to the ODN. The A "arm" moiety itself should be unreactive (other than through the leaving group L) under the conditions of hybridization of the ODN with the target DNA sequence, and should maintain the leaving group L in a desired steric position and distance from the desired site of reactions such as an N-7 position of a guanosine residue in the target DNA sequence. Generally speaking, the length of the A group should be equivalent to the length of a normal alkyl chain of approximately 2 to 50 carbons.

An exemplary more specific formula for a class of preferred embodiments of the cross-linking function is

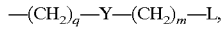

where L is the leaving group, defined above, each of m and q is independently 0 to 8, inclusive, and where Y is defined as a "functional linking group". A "functional linking group" is a group that has two functionalities, for example —$NH_2$ and —OH, or —COOH and —OH, or —COOH and —$NH_2$, which are capable of linking the $(CH_2)_q$ and $(CH_2)_m$ bridges. An acetylenic terminus (HC≡C—) is also a suitable functionality as a precursor for Y, because it can be coupled to certain heterocycles and therafter hydrogenated, as described below.

Other exemplary and more specific formulas for a class of preferred embodiments of the cross-linking function are

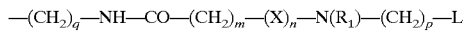

and

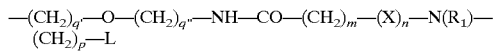

where q, m and L are defined as above, q' is 3 to 7 inclusive, q" is 1 to 7 inclusive, X is phenyl or simple substituted phenyl (such as chloro, bromo, lower alkyl or lower alkoxy substituted phenyl), n is 0 or 1, p is an integer from 1 to 6, and $R_1$ is H, lower alkyl or $(CH_2)_p$—L. Preferably p is 2. Those skilled in the art will recognize that the structure —N($R_1$)—$(CH_2)_2$—L describes a "nitrogen mustard", which is a class of potent alkylating agents. Particularly preferred are within the scope of the present invention are those modified ODNs where the cross-linking agent includes the functionality —N($R_1$—)$(CH_2)_2$—L where L is halogen, preferably chlorine; and even more preferred are those modified ODNs where the cross linking agent includes the grouping —N—$[(CH_2)_2$—$L]_2$ (a "bifunctional" N-mustard).

In accordance with one aspect of the present invention, the "bifunctional" N-mustard, (or other cross linking function having two reactive groups) is included in the cross-linking agent. One such cross-linking agent attached to the ODN is sufficient, as there is evidence in accordance with the present invention that after hybridization the modified ODN attaches to both strands of the target double stranded DNA sequence.

In accordance with another aspect of the present invention, cross-linking agents are attached to at least two different sites of the ODN. In this case also, evidence indicates that two separate covalent bonds are formed with the target DNA sequence. In both situations, in accordance with the invention, formation of at least two covalent bonds with the target DNA is required to attain substantial theraputic utility. A particularly preferred partial structure of the cross linking agent includes the grouping

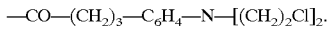

In a particularly preferred embodiment the just-noted cross-linking group is attached to an n-hexylamine bearing tail at the 5' and 3' ends of the ODN in accordance with the following structure:

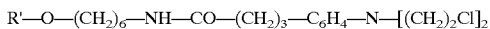

where R' signifies the terminal 5' or 3'-phosphate group of the ODN.

In accordance with other preferred embodiments, the cross-linking functionality is covalently linked to the heterocyclic base, for example to the uracil moiety of a 2'-deoxyuridylic acid building block of the ODN. The linkage can occur through the intermediacy of an amino group, that is, the "arm-leaving group combination" (A—L) may be attached to a 5-amino-2'-deoxyuridylic acid building unit of the ODN. In still other preferred embodiments the "arm-leaving group combination" (A—L) is attached to the 5-position of the 2'-deoxyuridylic acid building unit of the ODN by a carbon-to-carbon bond. Generally speaking, 5-substituted-2'-deoxyuridines can be obtained by an adaptation of the general procedure of Robins et al. (*J. Can. J. Chem.*, 60:554 (1982); *J. Org. Chem.*, 48:1854 (1983)), as shown in Reaction Scheme 1. In accordance with this adaptation, the palladium-mediated coupling of a substituted 1-alkyne to 5-iodo-2'-deoxyuridine gives an acetylene-coupled product. The acetylenic durd analog is reduced, with Raney nickel for example, to give the saturated compound, which is then used for direct conversion to a reagent for use on an automated DNA synthesizer, as described below. In Reaction Scheme 1 q is defined as above, and Y' is either Y (as defined above) or is a suitable protected derivative of Y. Y' can also be defined as a group which terminates in a suitably protected nuchleophilic function, such as a protected amine. Examples of reagents which can be coupled to 5-iodo-2'-deoxyuridine in accordance with this scheme are HC≡$CCH_2OCH_2CH_2N(CO)_2C_6H_4$ (phtalimidoethoxypropyne) and HC≡$CCH_2OCH_2CH_2NHCOCF_3$ (trifluoroacetamidoethoxypropyne).

In these examples the nucleosides which are obtained in this scheme are incorporated into the desired ODN, and the alkylating portion of the cross-linking agent is attached to the terminal amino group of "Y'" only after removal of the respective phtalic or trifluoroacetyl blocking groups.

4-d]pyrimidines, which are analogs of adenine, the crosslinking arm is attached at the 3-position, which is equivalent to the 7-position of purine.

The crosslinking side chain (arm=A) should be of sufficient length to reach across the major groove from a purine Reaction Scheme 1

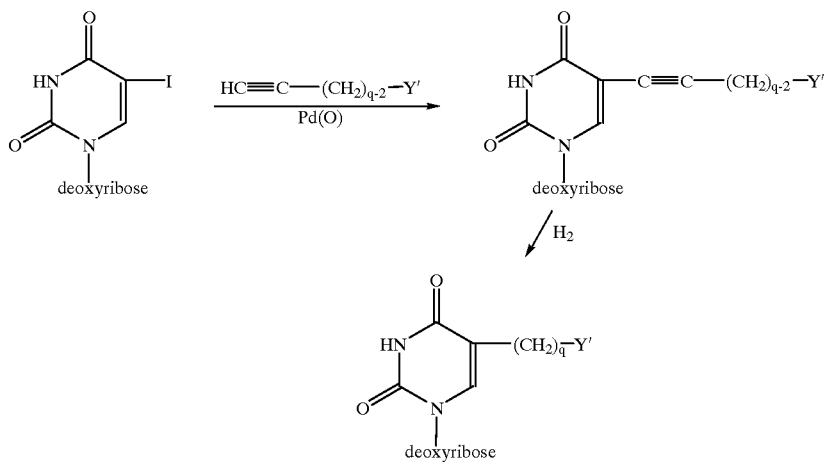

Other examples of nucleotides where the crosslinking agent is attached to a heterocyclic base, are 2'-deoxy-4-aminopyrazolo[3,4-d]pyrimidine derivatives. The general structure of these derivatives is shown below; A—L represents the "arm" and the "leaving group" of the cross-linking functionality, as described above.

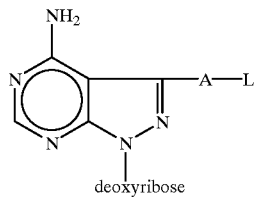

The above compounds can be made from 3,4-disubstituted and 3,4,6-trisubstituted pyrazolo[3,4-d] pyrimidines. The synthesis of these compounds is disclosed in commonly owned, copending application Ser. No. 353,857 filed on May 18, 1989 which is a continuation-in-part of application Ser. No. 250,474, filed on Sep. 28, 1988, the entire disclosure of which is incorporated herein by reference.

Discussing still in general terms the structures of the modified ODNs of the present invention, it is noted that examination of double-stranded DNA by ball-and-stick models and high resolution computer graphics indicates that the 7-position of the purines and the 5-position of the pyrimidines lie in the major groove of the B-form duplex of double-stranded nucleic acids. These positions can be substituted with side chains of considerable bulk without interfering with the hybridization properties of the bases. These side arms may be introduced either by derivatization of dThd or dCyd, or by straightforward total synthesis of the heterocyclic base, followed by glycosylation. These modified nucleosides may be converted into the appropriate activated nucleotides for incorporation into oligonucleotides with an automated DNA synthesizer. With the pyrazolo[3, 7- or 8-position, pyrimidine 5-position, pyrrolopyrimidine 5-position or pyrazolopyrimidine 3-position and reacting with the N-7 of a purine (preferably guanine) located above (on the oligomer 3'-side) the base pair containing the modified analog. The crosslinking side chain (arm=A) holds the functional group away from the base when the base is paired with another within the double-stranded complex. As noted above, broadly the arm A should be equivalent in length to a normal alkyl chain of 2 to 50 carbons. Preferably, the arms include alkylene groups of 1 to 12 carbon atoms, alkenylene groups of 2 to 12 carbon atoms and 1 or 2 olefinic bonds, alkynylene groups of 2 to 12 carbon atoms and 1 or 2 acetylenic bonds, or such groups substituted at a terminal point with nucleophilic groups such as oxy, thio, amino or chemically blocked derivatives thereof (e.g., trifluoroacetamido, phthalimido, CONR', NR'CO, and $SO_2NR'$, where $R'=H$ or $C_{1-6}$alkyl). Such functionalities, including aliphatic or aromatic amines, exhibit nucleophilic properties and are capable of serving as a point of attachment to such groups as

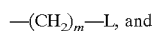

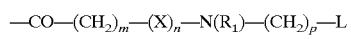

which are described above as components of examplary cross-linking functional groups.

To optimize strand crosslinking, it would be desirable to have the target strand base which is being attacked paired to the first or second base which is on the 3' side of the modified base in the oligonucleotide containing the crosslinking arm.

It has been found that when the modified base containing the crosslinking arm is a uracil and the target sequence is GGA, alkylation of the second guanine on the target's 5' side of the crosslinker-modified base pair is the exclusive action observed. The crosslinking reaction seems to be very specific for the "best fit" of electrophile to nucleophile, i.e., two or more guanine residues may need to neighbor the complement of the modified base to discover the site of alkylation.

In light of the foregoing, a general structure of the novel oligonucleotides (ODNs) of the present invention is represented by the formulas below,

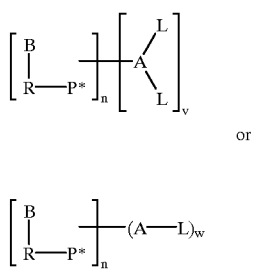

(i)

or $$\left[ \begin{array}{c} B \\ | \\ R-P^* \end{array} \right]_n \!\!-\!\! (A-L)_w$$

(ii)

where B—R—P* represents a nucleotide building block of the oligonucleotide. B—R—P* includes intermediate nucleotide units and the 5'- and 3' terminal nucleotide units. Specifically, B represents a heterocyclic base component of the nucleotide, R represents a sugar moiety which forms a pyranose of furanose ring, or an isosteric analog thereof, and P* represents a phosphate group included in a phosphate monoester, phosphate diester or phospate triester group, or P* represents a monothioate or dithioate analog of said phosphate groups. P* further includes the above-noted phosphate, phosphothioate or phosphodithioate groups in internucleotidic linkages, and also at the 5' and 3' terminus of the ologonucleotide, n is an integer with the values between 5 and approximately 50, v is 1–10;

w is between 2–10, preferably 2 (signifying that there are at least two alkylating groups);

the A—L grouping forms an electrophilic alkylating group such that L is a leaving group and A—L is inert under conditions of hybridization with the target sequence of DNA, in the sense that the group A—L does not react with the DNA (and with other reagents which may be present in the system under the conditions of hydrydization) until after hybridization and only when the "attacking" nucleophilic group (such as the N-7 of guanine) is in close proximity due to the hybridization. After hybridization A—L alkylates a nucleophilic site in the target sequence of DNA.

After the nucleoside or nucleotide unit which carries the crosslinking functionality A—L, or a suitable precursor thereof, (such as the —(CH$_2$)$_q$—NH$_2$ or —(CH$_2$)$_q$—Y group, where Y terminates with a nucleophilic group such as NH$_2$) is prepared, further preparation of the modified oligonucleotides of the present invention can proceed in accordance with state-of-the-art. Thus, to prepare oligonucleotides, protective groups are introduced onto the nucleosides or nucleotides and the compounds are activated for use in the synthesis of oligonucleotides. The conversion to protected, activated forms follows the procedures as described for 2'-deoxynucleosides in detail in several reviews. See, Sonveaux, *Bioorganic Chemistry*, 14:274–325 (1986); Jones, in "Oligonucleotide Synthesis, a Practical Approach", M. J. Gait, Ed., IRL Press, p. 23–34 (1984).

The activated nucleotides are incorporated into oligonucleotides in a manner analogous to that for DNA and RNA nucleotides, in that the correct nucleotides will be sequentially linked to form a chain of nucleotides which is complementary to a sequence of nucleotides in target DNA or RNA. The nucleotides may be incorporated either enzymatically or via chemical synthesis. The nucleotides may be converted to their 5'-O-dimethoxytrityl-3'-(N,N-diisopropyl) phosphoramidite cyanoethyl ester derivatives, and incorporated into synthetic oligonucleotides following the procedures in "Oligonucleotide Synthesis: A Practical Approach", supra. The N-protecting groups are then removed, along with the other oligonucleotide blocking groups, by post-synthesis aminolysis, by procedures generally known in the art.

In a preferred embodiment, the activated nucleotides may be used directly on an automated DNA synthesizer according to the procedures and instructions of the particular synthesizer employed.

The oligonucleotides may be prepared on the synthesizer using the standard commercial phosphoramidite or H-phosphonate chemistries.

A moiety containing the leaving group, such as a haloacyl group, or —CO—(CH$_2$)$_m$—(X)$_n$—N(R$_1$)—(CH$_2$)$_p$—L group (even more preferably a CO—(CH$_2$)$_3$—C$_6$H$_4$—N—[CH$_2$CH$_2$Cl]$_2$) may be added to the aminoalkyl or like tails (—CH$_2$)$_q$—Y) following incorporation into oligonucleotides and removal of any blocking groups. For example, addition of an a-haloacetamide may be verified by a changed mobility of the modified compound on HPLC, corresponding to the removal of the positive charge of the amino group, and by subsequent readdition of a positive charge by reaction with 2-aminoethanethiol to give a derivative with reverse phase HPLC mobility similar to the original aminoalkyl-oligonucleotide.

In the situations where the cross linking agent (A—L moiety) is attached to the 3' or 5' terminus of the oligonucleotide, for example by an alkylamine linkage of the formula —(CH$_2$)$_q$—Y (Y terminating in an amine), the oligonuclotide synthesis may be performed to first yield the oligonucleotide with said aminoalkyl tail, to which then an alkylating moiety, such as the above-noted haloacylgroup or —CO—(CH$_2$)$_m$—(X)$_n$—N(R$_1$)—(CH$_2$)$_p$—L is introduced.

As noted above, the modified ODN of the present invention hybridizes to the target DNA sequence. This is followed by cross-linkage which inactivates the target DNA sequence. Following triple strand formation and covalent crosslinkage, the modified target DNA no longer supports replication or transcription. Unlike all other lesions in DNA, however, this modification is much less likely to be repaired by the organism. Normally, crosslinked DNA is repaired by a combination of excision repair and homologous recombination. With crosslinked triple strand complexes, however, there will be no undamaged copies of the targeted gene to participate in recombination. By analogy with procaryotic models, the eucaryotic cell may attempt to use a misrepair (or SOS) pathway wherein the crosslink will be removed, but at the expense of mutagenesis. In such case, gene function is likely to be irreversibly silenced by the resultant mutations.

The use of recombination enzymes in combination with anti-gene ODNs significantly enhances the efficiency with which the single strand ODN "finds" its complementary target DNA sequence. Accordingly, the efficiency of triple strand formation is greatly increased when the anti-gene ODN is combined with a recombination enzyme (for instance, in a nucleoprotein complex).

Within the present invention, suitable target DNA sequences include defective structural genes and both up-stream and down-stream regulatory control sequences which are defective, or otherwise malfunctioning so that their deactivation brings about a therapeutically beneficial result. Target sequences also include genes of invading organisms, such as viral, fungi, parasites, bacteria and tumor cells. The regulatory sequences may be involved in either transcription or replication. The anti-gene ODN is determined and designed according to the target DNA sequence chosen for alteration of function, and has a sequence complementary to one of the two strands of the chosen target DNA.

In a particularly preferred embodiment, an antigene ODN is administered to a cell or a host, and upon entry to a target cell nucleus, the anti-gene ODN combines with recombination enzymes present within the nucleus. In an alternative embodiment, the anti-gene ODN and recombination enzyme are combined ex vivo and then administered to a cell or a host as a nucleoprotein filament. In this embodiment, it may be advantageous to administer the nucleoprotein filament in a liposome. Preferred recombination enzymes include procaryotic and eucaryotic recombination enzymes, such as recA, human recombinase and Drosophila recombinase, with human recombinase particularly preferred.

As it was noted above, experimental evidence proves that both of the minimum two cross-linking agents incorporated into the modified ODNs of the present invention actually react with the target DNA sequence, and that both strands of the target sequence are subsequently covalently linked and deactivated by the modified ODN. Deactivation of both strands results in substantially improved therapeutic utility compared to the situation when only one strand of the double stranded DNA is covalently linked to the modified ODN.

Another important use or application of the modified ODNs of the present invention is in the field of mapping large DNA molecules, and related analytical and investigative techniques in the fields of molecular biology, genetics and biochemistry. For example, the ability to chemically restrict or cleave long double-stranded DNA at unique sites 10–20 base pairs in length as been frequently discussed as a technique which could accelerate the human genome project by providing a means for physically mapping large DNA molecules. In accordance with the present invention a triple-stranded complex is allowed to form between a synthetic oligonucleotide (ODN) and a "complementary" 10–20 base long homopurine run in double-stranded DNA. Since the modified ODN of the present invention is appropriately appended with two alkylating agents, crosslinkage to two guanine residues on opposite strands of the duplex takes place. Crosslinks to guanine residues are known in the art to render the alkylated DNA susceptible to cleavage, for example through cleavage of the glycosidic bond between the alkylated guanine base and the sugar moiety, followed by cleavage of the phosphosdiester bond. The overall cleavage of the alkylated DNA at the alkylation sites may occur spontaneously, or as a result of an appropriate enzyme or other reagent acting on the modified DNA. In accordance with the presently preferred mode of the invention the alkylated duplex DNA is incubated with an amino acid, lysine, arginine or histidine, or with a DNA associating protein (such as a histone or a recombinase A enzyme). This converts each alkylation site into a cleavage site probably through the process of depurination (cleavage of glycosidic bond of the alkylated guanine residue) followed by beta elimination reaction.

More specifically, still in connection with the use of the modified ODNs of the present invention for "DNA mapping" or "gene mapping" or related investigatve procedures, the following is noted. The structure of the modified ODN used in the process is known in accordance with the present invention. Thus, the modified ODN can be tailor made to cleave at one or more specific approximately 10 to 20 base pair regions (target regions) of the target DNA. The structure of the target region may be known already, in which case the modified ODN is created specifically for the target region pursuant to the rules of Hoogsteen pairing, or possibly under the universal rules of base pairing if a recombinase enzyme is also used. In the following further description and examples however only "Hoogsteen pairing" is utilized. Alternatively, no specific site in the target DNA may be known, in which case the site of cleavage brought about as a result of hybridization with a modified ODN of known sequence nevertheless provides information about the existence and number of "matching" regions in the target DNA.

Thus, in accordance with this aspect of the invention and examples, a double-stranded plasmid DNA which contains a 20 base pair long homopurine/homopyrimidine run is chemically restricted. To effect cleavage 1–10 $\mu$g of the plasmid is incubated with 1–10 $\mu$M of a $C^+$/T, G/A or G/T motif 20 mer ODN designed to form a sequence specific triple strand with the homopurine run using the Hoogsteen base pairing rules. (For an A rich homopurine run a $C^+$/T or G/A motif ODN is employed; for a G rich homopurine run a G/A or G/T motif ODN is used.) Triplexing is carried out overnight at 15–37° C. in the presence of 10 mM $MgCl_2$ at pH 6.0 ($C^+$/T motif) or pH 7.0–7.5 (G/A or G/T motif). The $C^+$symbol in the $C^+$/T motif stands for 5-methylcytosine base which is better suited for Hoogsteen pairing than cytosine.

The modified ODN which becomes the third strand during the incubation may have the two alkylating groups appended to either internal base residues or to the 5' or 3' terminus. Each alkylating group reacts with the N-7 position of a nearby guanine residue of the targeted duplex. Double standed break of the duplex occurs because the two guanine residues reside on opposite strands of the duplex. In the case where the alkylating group is attached to an internal base on the third strand ODN, that base is purposely designed to form a mismatch with the opposing G-C or C-G base pair in the targeted duplex. This allows access to the N-7 position of guanine by the alkylator. By contrast, when the alkylating group is attached to the end of the ODN so as to target a guanine residue in the flanking duplex, the terminal base in the ODN is designed to hydrogen bond to the opposing base pair of the target. The general rules for placement of alkylating groups on the ODNs are illustrated by the three examples below where the upper strand is the crosslinkable third strand ODN; X represents a terminal alkylating group while Y represents an alkylating group attached to an internal 3-aminopropyl-deoxyuridine residue. The guanine bases crosslinked in the target duplex are bold faced and underlined. The crosslinkable ODN is identified by a Sequence No. and the double stranded target, is also identified by a single Sequence No.

EXAMPLE 1

G/A motif ODN targeted to the homopurine run in human HLA DQBL 0302 allele:

3'-XGAGAGAGGAAAGAGGAGAX     Sequence No. 1

5'-ATATAAGGAGAGAGGAAAGAGGAGACAAA

3'-TATATTCCTCTCTCCTTTCTCCTCT<u>G</u>TTT     Sequence No. 2

EXAMPLE 2

G/T motif ODN targeted to the homopurine run in human epidermal growth factor receptor:

3'-GGGTGGTGYTGTGYTGGTGGTGTT     Sequence No. 3

5'-GGGAGGAGCAGAG<u>G</u>AGGAGGAGAA

3'-CCCTCCTCGTCTCCTCCTCCTCTT    Sequence No. 4

EXAMPLE 3

C+/T/G motif ODN targeted to a homopurine run in HIV proviral DNA:

5'-TTTTCTTTTYGGGGGTX    Sequence No. 5

5'-TTTTTAAAAGAAAAGGGGGACTGG

3'-AAAAATTTTCTTTTCCCCCCTGACC    Sequence No. 6

After complexing the modified ODN to the target duplex and cross-linking the crosslinked DNA is incubated 12–24 hr at 37° with 10 mM lysine, arginine or histidine. As noted above, as a result of this procedure each crosslink is converted into a nick through a depurination and beta-elimination pathway. If the alkylated guanines are within 5–6 base pairs of one another the staggered nicks break the DNA;

otherwise, breakage is be accomplished by brief incubation with exonuclease III (3' to 5' digestion) or calf spleen phosphodiesterase (5' to 3' digestion) to remove a portion of the intervening duplex. The choice of exonuclease depends upon the polarity of the target strands in relation to the positions of the nicks. If necessary, prior to exonuclease treatment the triplex can be destroyed by complexing magnesium ion with excess EDTA and then spinning the sample through a disposable gel filtration cartridge. The spin simultaneously removes the ODN and exchanges the plasmid into exonuclease buffer. After digestion the samples can be phenol extracted and alcohol precipitated for use in later experiments.

Specific Embodiments and Experimental Procedures General

"RT" in this experimental description means room temperature. Thin layer chromatography was performed on silica gel 60 F 254 plates (Analtech) using the following solvent mixtures: A-90% methylene chloride:10% methanol; B-50% ethyl acetate:50% hexanes; C-70% ethyl acetate: 10% methanol:10% water:10% acetone; D-50% ether:50% hexanes. Flash chromatography was performed using 60 F 254 silica (Merck). Oligonucleotides were synthesized on an Applied Biosystems Model 380B Synthesizer. Oligonucleotides were isotopically labeled using T4 Polynucleotide kinase (BRL) and $\tau$-$^{32}$P-ATP (New England Nuclear).

5-(4-Phthalimidobut-1-yn-1-yl)-2'-deoxyuridine

5-Iodo-2'-deoxyuridine (354 mg, 1 mmol) was dissolved in 10 mL of dimethylformamide. Cuprous iodide (76 mg, 0.4 mmol), tetrakis(triphenylphosphine)palladium(0) (230 mg, 0.2 mmol), and triethylamine (200 mg, 2.0 mmol) were added. 4-Phthalimidobut-1-yne (300 mg, 1.5 mmol) was added all at once and the reaction kept at 60° C. for three hours. The clear yellow reaction was then evaporated and methylene chloride was added. Scratching of the flask induced crystallization of nearly all of the product which was filtered and recrystallized from 95% ethanol to give 335 mg (78%) of title compound as fine, feathery needles.

5-(4-Phthalimidobut-1-yl)-2'-deoxyuridine 1.00 Gram of 5-(4-Phthalimidobut-1-yn-1-yl)-2'-deoxyuridine was dissolved in 95% EtOH and about 3 g of neutral Raney nickel was added. After 48 hours, the catalyst was removed by cautious filtration and the filtrate was evaporated to a solid which was recrystallized from methanol-water to give 960 mg (97%) of the title compound.

5-(4-(4-Bromobutyramido)butyl)-2'-deoxyuridine 5-(4-phthalimidobut-1-yl)-2'-deoxyuridine is treated with ammonia and then with N-hydroxysuccinimidyl-4-bromobutyrate to give 5-(4-(4-bromobutyramido)butyl)-2'-deoxyuridine.

2,3,5,6-Tetrafluorophenyl trifluoroacetate

A mixture of 2,3,5,6-tetrafluorophenol (55.2 g, 0.33 mol), trifluoroacetic anhydride (60 mL, 0.42 mol) and boron trifluoride etherate (0.5 mL) was refluxed for 16 hr. Trifluoroacetic anhydride and trifluoroacetic acid were removed by distillation at atmospheric pressure. The trifluoroacetic anhydride fraction (bp 40° C.) was returned to the reaction mixture along with 0.5 mL of boron trifluoride etherate, and the mixture was refluxed for 24 hr. This process was repeated two times to ensure complete reaction. After distillation at atmospheric pressure, the desired product was collected at 62° C./45 mm (45° C./18 mm) as a colorless liquid: yield=81.3 g (93%); d=1.52 g/mL; $n_D^{21}$=1.3747; IR (CHCl$_3$) 3010, 1815, 1525, 1485, 1235, 1180, 1110, and 955 cm$^{-1}$. Anal. Calcd for C$_8$HF$_7$O$_2$: C, 36.66; H, 0.38; F, 50.74. Found: C, 36.31; H, 0.43; 30 F, 50.95.

2,3,5,6-Tetrafluorophenyl-4'-[bis(2-chloroethyl)aminolphenylbutyrate (Chlorambucil 2,3,5,6-tetrafluorophenyl ester)

To a solution of 0.25 g (0.82 mmol) of chlorambucil (supplied by Fluka A. G.), 0.3 g (1.1 mmol) of 2,3,5,6-tetrafluorophenyl trifluoroacetate in 5 ml of dry dichloromethane was added 0.2 Ml of dry triethylamine. The mixture was stirred under argon at room temperature for 0.5 h and evaporated. The residual oil was purified by column chromatography on silica gel with hexane-chloroform (2:1) as the eluting solvent to give the ester as an oil: 0.28 g (75%); TLC on silica gel (CHCl$_3$) R$_f$ 0.6; IR (in CHCl$_3$) 3010, 1780, 1613, 1521, 1485 cm$^{-1}$.

2-Proparqyloxtethyl)amine (John, R., and Seitz, G., Chem. Ber., 123, 133 (1990) was prepared by condensing propynol with 2-bromoethylammonlum bromide in liquid ammonia in the presence of Na NH$_2$, and was used crude for the next reaction.

3-(2-Trifluoroacetamidoethoxv)propyne (2-Propargyloxyethyl)amine (13.8 g, 0.14 mol) is stirred and chilled in an iso-propanol-dry ice bath while excess of trifluoroacetic anhydride (26 ml, 0.18 mol) is added dropwise. N-(2-Propargyloxyethyl)trifluoroacetamide is distilled at 84–85°/1.7 torr as an oil which solidified upon refrigeration; yield 14.4 g (52%), m.p. (16°, $n_p^{24}$ 1.4110. Anal. Calcd. for C$_7$H$_8$F$_3$NO$_2$: C, 43.09, H, 4.13; N, 7.18; F, 29.21. Found: C, 42.80; H, 4.03; N, 7.06; F, 29.38.

5-[3-(2-Trifluoroacetamidoethoxy)propynyl]-2'-deoxyuridine

A mixture of 5-iodo-2'-deoxyuridine (3.54 g, 10 mmol), copper(1) iodide (0.19 g, 1 mmol) and tetrakis (triphenylphosphine)palladium(O) (0.58 g, 0.5 mmol) is dried in vacuo at 60° for 3 hours and placed under argon. A suspension of the mixture in dry DMF (20 ml) is stirred under argon and treated with dry triethylamine (1.7 ml, 12 mmol) followed by 3-(2-Trifluoroacetamidoethoxy)propyne (3.17 g, 16 mmol). The mixture is cooled at room temperature water bath and stirred for 17 hours. The mixture is treated with 2% acetic acid (100 ml), the catalyst is removed by filtration and washed with 50% methanol. The filtrates are combined and passed onto a LiChroprep RP-18 column (5×25 cm), the column is washed, then eluted with 1% acetic acid in 50% (v/v) methanol. The fractions with the main produce are combined, evaporated, and dried in vacuo. The resultant foam is stirred with 150 ml of ether to give crystalline product; yield 3.6 g (85%); m.p. 145–152°.

5-[3-(2-Trifluoroacetamidoethoxy)propyl]2'-deoxyuridine

A solution of 5-[3-(2-trifluoroacetamidoethoxy) propynyl]-2'-deoxyuridine (3.4 g, 8.1 mmol) in methanol (20 ml) is stirred with ammonium formate (prepared by addition of 3 ml, 79 mmol of cold 98% formic acid into 2 ml, 50 mmol of dry ice frozen 25% ammonia) and 0.2 g of 10% Pd/C for 7 hours at room temperature under hydrogen atmosphere. The catalyst is removed by filtration, the filtrate evaporated and product is purified on LiChroprep RP-18 column by the above procedure. Fractions containing the desired product are combined and evaporated to dryness in vacuo and the resultant solid is triturated with dry ether to give 3.0 g (87% product, m.p. 107–110°; max in nm, in 0.1M triethylamine-acetate (pH 7.5), 220, 268. Analysis calculated for $C_{16}H_{22}F_3N_3O_7$: C, 45.18; H, 5.21; N, 9.88; F, 13.40. Found C, 45.16; H, 5.16; N, 9.68; F, 13.13.

Preparation of Synthetic Oligonucleotides Phosphoramidite Preparation and DNA Synthesis.

Nucleosides were 5'-dimethoxytritylated, following known procedures, to give around 85% yield, and the 3'-phosphoramidite was made using diisopropylamino—cyanoethylchlorophosphite (as described in "Oligonucleotide Synthesis: A Practical Approach", supra) with diisopropylethylamine in methylene chloride. The phosphoramidite was made into a 0.2N solution in acetonitrile and placed on the automated DNA synthesizer. Incorporation of these new and modified phosphoramidites gave incorporation similar to ordinary phosphoramidites (97–99% as judged by assay of the trityl color released by UV.)

Oligonucleotides were removed from the DNA synthesizer in tritylated form and deblocked using 30% ammonia at 55° C. for 6 hours. Ten $\mu$L of 0.5M sodium bicarbonate was added to prevent acidification during concentration. The oligonucleotide was evaporated to dryness under vacuum and redissolved in 1.0 mL water. The oligonucleotides were purified by HPLC using 15–55% acetonitrile in 0.1N triethylammonium acetate over 20 minutes. Unsubstituted oligonucleotides came off at 10 minutes; amino derivatives took 11–12 minutes. The desired oligonucleotide was collected and evaporated to dryness, then it was redissolved in 80% aqueous acetic acid for 90 minutes to remove the trityl group.

Desalting was accomplished with a G25 Sephadex column and appropriate fractions were taken. The fractions were concentrated, brought to a specific volume, dilution reading taken to ascertain overall yield and an analytical HPLC done to assure purity. Oligonucleotides were frozen at 20° C. until use.

Introduction of chlorambucil residue into the primary amino groups of oligonucleotides Preparation of the cetyltrimethylammonium salt of oligonucleotides: a 100 $\mu$L of aqueous solution of oligonucleotide (50–500 ug), generally triethylammonium salt, was injected to a column packed with Dowex 50w×8 in the cetyltrimethylammonium form and prewashed with 50% alcohol in water. The column was eluted by 50% aqueous ethanol (0.1 mL/min). Oligonucleotide containing fraction was dried on a Speedvac over 2 hours and used in following reactions.

Ethanol solution (50 uL) of cetyltrimethylammonium salt of an oligonucleotide (50–100 $\mu$g) was mixed with of 0.08 M solution of 2,3,5,6-tetrafluorophenyl-4'-[bis(2-chloroethyl)amino]phenylbutyrate (tetrafluorophenyl ester of chlorambucil) in acetonitrile (50 $\mu$L) and 3 $\mu$L of diisopropylethylamine. After shaking for three hours at room temperature, the product was precipitated by 2% $LiClO_4$ in acetone (1.5 mL). The product was reprecipitated from water (60 uL) by 2% $LiClO_4$ in acetone three times. Finally chlorambucil derivative of oligonucleotide was purified by Reverse Phase Chromatography with approximately 50–80% yield. The fraction containing a product was concentrated by approximately butanol. Isolated chlorambucil derivative of oligonucleotide was precipitated in acetone solution of $LiClO_4$, washed by acetone and dried under vacuum of oil pump. All manipulation of reactive oligonucleotide was performed as quickly as possible, with the product in ice-cold solution, starting from the chromatographic fraction collected.

Demonstration of crosslinking of the third-strand oligonucleotide to both strands of a duplex DNA target within a triplex The following sequences were used to demonstrate bifunctional crosslinking:

C: 5'-XCTTTCCTCTCTTTTCCCCX-3'  Seq. 7

A: 5'-AAATACTGGGAGAAAGGAGAGAAAAGGG-GACCCAACGTAT-3'

B: 3'-TTTATGACCCTCTTTCCTCTCTTTTC-CCCTGGGTTGCATA-5'  Seq. 8

The strands A and B form the Watson-Crick duplex by conventional base pairing, and C is the third strand, which pairs to strand A within the duplex by Hoogsteen hydrogen bonding. The X residues in strand C bear the alkylating moiety which is shown by the formulas below. In this example, the p-[bis(2-chloroethyl)amino]phenylbutyrate group (designated CA) is bound to, in one case, a 5-(aminoethoxypropyl)deoxyuridine, which is the terminal nucleotide at either the 3'- or 5'-end, or at both ends, of the oligoncueotide C. In the second case, the alkylating group (CA) is bound to an aminohexyl group esterified to a phosphate at either the 3'- or 5'-end, or to both ends, of the oligonucleotide. The alkylating residue CA is placed onto the reactive amino group of the oligonucleotide by the method described above. Oligonucleotides were labeled with [-$^{32}$P]ATP from DuPont (NEN Research Products; Boston, Mass.) and T4 polynucleotide kinase from United States Biochemical (Cleveland, OH) using the procedure of Maxam and Gilbert (Maxam,A. M.;Gilbert,W. (1980) Methods in Enzymology, 65, 499). The $^{32}$P-labeled product was purified using Dupont Nensorb™ 20 columns (Wilmington, Del.). Cerenkov counting was done on a Beckman LS 5000TD from Beckman Instruments, Inc. (Fullerton, Calif.). Oligonucleotide concentrations were calculated from $A_{260}$ values.

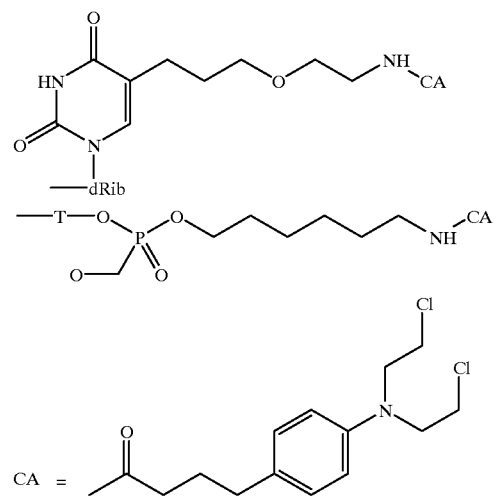

Each hybridization mixture contained 5 $\mu$L of the labelled oligonucleotide in water, conc $5\times10^{-7}$ M, was mixed with 10

μL of complementary unlabelled strand, at the same conc, and with 5 μL of a buffer which contained 350 mM NaCl, 100 mM MgCl$_2$, and 125 mM Na cacodylate, pH 6.0. After mixing, the mixture was incubated at 37° for 1 hr, and then 5 μL of a solution of reactive oligonucleotide (which had been kept ice-cold until this time), conc 5×10$^{-5}$, was added, and incubation was continued at 37° for various times. The drawing figure depicting results of an electrophoresis shows the formation of the slower moving bands that correspond to all three strands in the system being covalently linked together, indicating bifunctional crosslinking.

To show the sites of cleavage, the mixture was run on 5% denaturing polyacrylamide gel electrophoresis with 8M urea, 90 mM Tris-borate, and 2 mM EDTA, pH 8.2. The position of cleavage was ascertained by treatment of the incubation mixtures with 1 M pyrrolidine in water for 15 min, 2× evaporation from water, and then polyacrylamide gel electrophoresis on a 20% gel. This analysis showed specific cleavage of the labeled target strand at the expected site, which was the guanines in the flanking area of the strand C binding site; specifically, the guanines immediately 5' to the strand C binding site on both strands A and B, which are indicated in the diagram of the strands by underlining.

What is claimed is:

1. A modified oligonucleotide which is complementary to a target sequence of nucleotides in duplex DNA, the oligonucleotide comprising:

approximately 5 to 50 nucleotide units connected to one another by phosphate, phosphorothioate or phosphorodithioate linkages, each nucleotide unit comprising a heterocyclic base and a sugar moiety or an isosteric equivalent of a sugar attached to the heterocyclic base;

at least two cross-linking agents covalently attached to the oligonucleotide, each cross-linking agent having the structure A—L, where L is an electrophilic leaving group and where A is a group covalently bonding the L group to the oligonucleotide, wherein the oligonucleotide hybridizes with the target sequence in the duplex DNA when the oligonucleotide contacts the duplex DNA, and after hybridization the A—L groups react with nucleophilic sites in both strands of the target sequence in the duplex DNA, whereby after hybridization the modified oligonucleotide becomes covalently linked to both strands of the target sequence.

2. The modified oligonucleotide of claim 1 wherein the cross-linking agents A—L are attached to the heterocyclic bases.

3. The modified oligonucleotide of claim 2 wherein A—L is a group selected from the groups consisting of —(CH$_2$)$_q$—Y—((CH$_2$)$_m$—L
—(CH$_2$)$_q$—NH—CO—(CH$_2$)$_m$—(X)$_n$—N(R$_1$)—(CH$_2$)$_p$—L, and
—(CH$_2$)$_{q'}$—O—(CH$_2$)$_{q''}$—NH—CO—(CH$_2$)$_m$—(X)$_n$—N(R$_1$)—(CH$_2$)$_p$—L where each of m and q is independently 0 to 8, inclusive, q' is 3 to 7 inclusive, q" is 1 to 7 inclusive, Y is a linking group derived from a bifunctional molecule having a hydrocarbyl backbone and having at each end a functionality selected from —NH$_2$, —OH, SH, —COOH and C≡CH, and X is phenyl, or phenyl substituted with chloro, bromo, lower alkyl or lower alkoxy groups, n is 0 or 1, p is an integer from 1 to 6, and R$_1$ is H, lower alkyl or (CH$_2$)$_p$—L.

4. The modified oligonucleotide of claim 3 wherein the cross-linking agents A—L are attached to the 5-position of uracil bases.

5. The modified oligonucleotide of claim 4 wherein the A—L group is

—(CH$_2$)$_3$O(CH$_2$)$_2$NHCO(CH$_2$)$_3$—C$_6$H$_4$—N—[CH$_2$CH$_2$Cl]$_2$.

6. The modified oligonucleotide of claim 1 wherein the A—L group is equivalent in length to a normal alkyl chain of approximately 2 to 50 carbons.

7. The modified oligonucleotide of claim 1 wherein the cross-linking agents A—L are attached to phosphate groups.

8. The modified oligonucleotide of claim 7 wherein the modified oligonucleotide has a 3' and a 5' phosphate terminus, and wherein the cross linking agents A—L are attached to the 3' and 5' phosphate termini.

9. The modified oligonucleotide of claim 7 herein A—L is a group selected from the groups consisting of —(CH$_2$)$_q$—Y—((CH$_2$)$_m$—L,
—(CH$_2$)$_q$—NH—CO—(CH$_2$)$_m$—(X)$_n$—N(R$_1$)—(CH$_2$)$_p$—L, and
—(CH$_2$)$_{q'}$—O—(CH$_2$)$_{q''}$—NH—CO—(CH$_2$)$_m$—(X)$_n$—N(R$_1$)—(CH$_2$)$_p$—L where each of m and q is independently 0 to 8, inclusive, q' is 3 to 7 inclusive, q" is 1 to 7 inclusive, Y is a linking group derived from a bifunctional molecule having a hydrocarbyl backbone and having at each end a functionality selected from —NH$_2$, —OH, SH, and —COOH, and X is phenyl, or phenyl substituted with chloro, bromo, lower alkyl or lower alkoxy groups, n is 0 or 1, p is an integer from 1 to 6, and R$_1$ is H, lower alkyl or (CH$_2$)$_p$—L.

10. The modified oligonucleotide of claim 9 wherein the A—L group is

—(CH$_2$)$_3$O(CH$_2$)$_2$NHCO(CH$_2$)$_3$—C$_6$H$_4$—N—[CH$_2$CH$_2$Cl]$_2$.

11. The modified oligonucleotide of claim 1 wherein the L group is selected from a group consisting of chloro, bromo, iodo, SO$_2$R''', and S$^+$R'''R'''', where each of R''' and R'''' is independently C$_{1-6}$alkyl or aryl or R''' and R'''' together form a C$_{1-6}$alkylene bridge.

12. A modified oligonucleotide having the structure (i) or (ii)

or

wherein B represents a heterocyclic base, R represents a sugar moiety in pentofuranosyl, hexofuranosyl, pentopyranosyl or hexopyranosyl form, or an isosteric equivalent of said sugars, the sugar being linked to the heterocyclic base to form a nucleoside therewith, P* represents a phosphate monoester, phosphate diester, phosphate triester, or a monothioate or dithioate of said phosphate groups, the P* groups being linked to the R groups and forming the linkages between the individual nucleoside units, n is an integer having the values 5 to 50, inclusive;

v is an integer having the values of 1–10, inclusive;

w is an integer having the values of 2–10 inclusive;

the A—L and A—$L_2$ groups are electrophilic alkylating groups, wherein L is a leaving group selected independently from a group consisting of chloro, bromo, iodo, $SO_2R'''$, and $S+R'''R''''$, where each of R''' and R'''' is independently $C_{1-6}$alkyl or aryl or R''' and R'''' together form a $C_{1-6}$alkylene bridge, and A is a group covalently bonding the L group to B, R, or P* groups, the A group being substantially equivalent in length to a normal alkyl chain having 2 to 50 carbons, wherein the modified oligonucleotide hybridizes with a target sequence in duplex DNA when the oligonucleotide contacts the duplex DNA, and after hybridization the A—L and A—$L_2$ groups react with nucleophilic sites in both strands of the target sequence in the duplex DNA, whereby after hybridization the modified oligonucleotide becomes covalently linked to both strands of the target sequence.

13. The modified oligonucleotide of claim 12 which is represented by the structure (i).

14. The modified oligonucleotide of claim 13 wherein the A—$L_2$ group is selected from the group consisting of

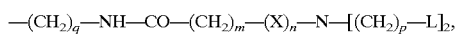

and

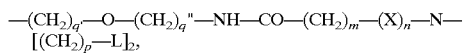

where each of m and q is independently 0 to 8, inclusive, q' is 3 to 7 inclusive, q'' is 1 to 7 inclusive, and X is phenyl, or phenyl substituted with chloro, bromo, lower alkyl or lower alkoxy groups, n is 0 or 1, p is an integer from 1 to 6.

15. The modified oligonucleotide of claim 14 wherein the A—$L_2$ group is attached to a heterocyclic base.

16. The modified oligonucleotide of claim 14 wherein the A—$L_2$ group is attached to a phosphate moiety.

17. The modified oligonucleotide of claim 13 comprising at least two A—$L_2$ groups.

18. The modified oligonucleotide of claim 17 wherein one A—$L_2$ group is attached to each terminal nucleotide unit of the oligonucleotide.

19. A method for inhibiting expression of a target sequence of nucleotides in the double stranded DNA which had been extracted from an organism or cell, the method comprising the step of contacting a modified oligonucleotide with a recombinase enzyme before the modified oligonucleotide is contacted with the double stranded DNA wherein the modified oligonucleotide is complementary in the Watson Crick sense to a target sequence of nucleotides in the duplex DNA, the oligonucleotide comprising:

approximately 5 to 50 nucleotide units connected to one another by phosphate, phosphorothioate or phosphorodithioate linkages, each nucleotide unit comprising a heterocyclic base and a sugar moiety or an isosteric equivalent of a sugar attached to the heterocyclic base;

at least two cross-linking agents covalently attached to the oligonucleotide, each cross-linking agent having the structure A—L, where L is an electrophilic leaving group and where A is a group covalently bonding the L group to the oligonucleotide, wherein the oligonucleotide hybridizes with the target sequence in the duplex DNA when the oligonucleotide contacts the duplex DNA, and after hybridization the A—L groups react with nucleophilic sites in both strands of the target sequence in the duplex DNA, whereby after hybridization the modified oligonucleotide becomes covalently linked to both strands of the target sequence, and wherein said recombinase enzyme facilitates the hybridization of the modified oligonucleotide with the target sequence.

20. A method for cleaving a target double stranded DNA that has been extracted from a cell or organism, at specific sites of substantially predetermined target sequence, the method including the step of incubating in the presence of a recombinase enzyme the target duplex DNA with a modified oligonucleotide which is complementary in the Watson Crick sense to a target sequence of nucleotides in the duplex DNA, the oligonucleotide comprising:

approximately 5 to 50 nucleotide units connected to one another by phosphate, phosphorothioate or phosphorodithioate linkages, each nucleotide unit comprising a heterocyclic base and a sugar moiety or an isosteric equivalent of a sugar attached to the heterocyclic base;

at least two cross-linking agents covalently attached to the oligonucleotide, each cross-linking agent having the structure A—L, where L is an electrophilic leaving group and where A is a group covalently bonding the L group to the oligonucleotide, wherein the oligonucleotide hybridizes with the target sequence in the duplex DNA when the oligonucleotide contacts the duplex DNA, and after hybridization the A—L groups react with nucleophilic sites in both strands of the target sequence in the duplex DNA, whereby after hybridization the modified oligonucleotide becomes covalently linked to both strands of the target sequence.

21. The modified oligonucleotide in accordance with claim 1 where the A—L group includes the moiety —$C_6H_4$—N—$(CH_2$—$CH_2$—$Cl)_2$, where Cl represents the L group.

22. The modified oligonucleotide in accordance with claim 3 where X is —$C_6H_4$, n is 1, $R_1$ is $(CH_2)_p$—L, p is 2 and L is Cl.

23. The modified oligonucleotide in accordance with claim 3 where the CO—$(CH_2)_m$—$(X)_n$—$N(R_1)$—$(CH_2)_p$—L group represents

24. The modified oligonucleotide in accordance with claim 13 where the A—L group includes the moiety —$C_6H_4$—N—$(CH_2$—$CH_2$—$Cl)_2$, where Cl represents the L group.

25. The modified oligonucleotide in accordance with claim 14 where X is — $C_6H_4$, n is 1, p is 2and L is Cl.

26. The method in accordance with claim 19 where A—L group of the modified oligonucleotide includes the moiety —$C_6H_4$—N—$(CH_2$—$CH_2$—$Cl)_2$, where Cl represents the L group.

27. The method in accordance with claim 19 where A—L group of the modified oligonucleotide includes the moiety CO—$(CH_2)_m$—$(X)_n$—$N(R_1)$—$(CH_2)_p$—L where m is 0 to 8, X is phenyl, or phenyl substituted with chloro, bromo, lower alkyl or lower alkoxy groups, n is 0 or 1, p is an integer from 1 to 6, and $R_1$ is H, lower alkyl or $(CH_2)_p$—L.

28. The method in accordance with claim 27 where X is —$C_6H_4$, n is 1, $R_1$ is $(CH_2)_p$—L, p is 2 and L is Cl.

29. The method in accordance with claim 28 where m is 3.

30. A method for cleaving a target double stranded DNA that has been extracted from a cell or organism, at specific sites of substantially predetermined target sequence, the method including the step of incubating the target duplex DNA with a modified oligonucleotide which is complementary under the rules of Hoogsteen pairing to a target sequence of nucleotides in the duplex DNA, the oligonucleotide comprising:

approximately 5 to 50 nucleotide units connected to one another by phosphate, phosphorothioate or phosphorodithioate linkages, each nucleotide unit comprising a heterocyclic base and a sugar moiety or an isosteric equivalent of a sugar attached to the heterocyclic base;

at least two cross-linking agents covalently attached to the oligonucleotide, each cross-linking agent having the structure A—L, where L is an electrophilic leaving group and where A is a group covalently bonding the L group to the oligonucleotide, wherein the oligonucleotide hybridizes with the target sequence in the duplex DNA when the oligonucleotide contacts the duplex DNA, and after hybridization the A—L groups react with nucleophilic sites in both strands of the target sequence in the duplex DNA, whereby after hybridization the modified oligonucleotide becomes covalently linked to both strands of the target sequence.

* * * * *